(12) United States Patent
Saji et al.

(10) Patent No.: US 6,392,093 B1
(45) Date of Patent: May 21, 2002

(54) PROCESS FOR THE OXIDATION OF CYCLOHEXANE TO ADIPIC ACID

(75) Inventors: Puthusseril Varkey Saji; Chandra Ratnasamy; Sarada Gopinathan, all of Maharastra (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/715,928

(22) Filed: Nov. 17, 2000

Related U.S. Application Data

(63) Continuation of application No. 09/034,202, filed on Mar. 3, 1998, now abandoned.

(30) Foreign Application Priority Data

Nov. 21, 1997 (IN) ........................................ 3358 Del/97

(51) Int. Cl.$^7$ .............................................. C07C 51/31
(52) U.S. Cl. ..................................................... 562/543
(58) Field of Search ......................................... 562/543

(56) References Cited

U.S. PATENT DOCUMENTS 5,093,491 A * 3/1992 Ellis, Jr. et al. ............ 540/135
5,672,778 A * 9/1997 Lyons et al. ................ 568/835

OTHER PUBLICATIONS

Balkus et al., Oxidations catalyzed by ship–in–a–bottle complexes, Aug. 1996, Applied Catalysis A: General V143 N.1, pp. 159–173.*

* cited by examiner

Primary Examiner—Rosalynd Keys
(74) Attorney, Agent, or Firm—Schweitzer Cornman Gross & Bondell LLP

(57) ABSTRACT

The present invention relates to an improved process for the oxidation of cyclohexane to adipic acid using air as an oxidant and a solid organotransition metal complex as a catalyst. The process comprises comprises reacting cyclohexane with air in the presence of a solid catalyst containing an encapsulated salen or substituted salen metal complex wherein some of the hydrogen atoms of the said organomanganese complex have been substituted by one or more electron withdrawing groups, at a temperature in the range of 20 to 120° C., at a pressure in the range of 50 to 1000 psi, in the presence or absence of solvents, with or without a promoter and isolating the adipic acid formed by conventional methods, such as filtration and centrifugation.

16 Claims, No Drawings

PROCESS FOR THE OXIDATION OF CYCLOHEXANE TO ADIPIC ACID

This application is a continuation of our application Ser. No. 09/034,202, filed Mar. 3, 1998, now abandoned.

The present invention relates to an improved process for the preparation of adipic acid. More particularly the present invention relates to an improved process for the preparation of adipic acid by the oxidation of cyclohexane, using air an an oxidant and a solid organotransition metal complex as a catalyst.

BACKGROUND

Adipic acid is industrially the most important dicarboxylic acid, used in the manufacture of polyamide nylon 6,6, urethane foams, acidulant in baking powder, in plastics and lubricating additives. The great majority of adipic acid on the market is made from cyclohexane, generally via KA oil which is mixture of cyclohexanol and cyclohexanone. Adipic acid is made by a two step process from cyclohexane. In the first step cyclohexane is oxidized at a temperature range 150 to 175° C. and a pressure of 115 to 175 psi in the presence of a soluble catalyst like cobalt napthenate or octoate in a concentration of 0.3 to 3 ppm. Conversions are usually in the range of 3 to 8% with selectivities in the range of 70 to 80%. In the second step, the mixture of cyclohexanol and cyclohexanone, which are formed by the oxidation of cyclohexane in the first step, are oxidized by nitric acid to adipic acid. Numerous byproducts are formed. The byproducts include formic, butyric, valeric and caproic acids. In addition gaseous byproducts like carbon monoxide and dioxide are also formed.

There are many drawbacks in the two-step process for the oxidation of cyclohexane to adipic acid mentioned hereinabove and in commercial practice worldwide extensively. One drawback is the low level (3–5%) of cyclohexane conversion necessiating the large recycle (more than 95%) of unreacted cyclohexane incurring thereby an expenditure of a large amount of process energy. A second major disadvantage of such process is the use of nitric acid in the oxidation of KA oil to adipic acid. Large amounts (mole equivalent of nitric acid used) of nitrogen oxide vapors are released in the process which constitute an environmental hazard. Yet another drawback of the two step prior art process is the large amount of liquid and gaseous by-products formed in both steps of the process leading to severe problems in their disposal. Eventhough many of these processes are practiced commercially, all of them suffer from high cost due to both such multi step operations and the use of nitric acid as well as from pollution problems caused by the discharge of ozone depleting nitrogen oxide byproducts mentioned hereinabove.

Other process options for the manufacture of adipic acid without the use of nitric acid have been proposed as for example in U.S. Pat. No. 3,390174 and British patent No. 1,304,855. However, the air oxidation processes proposed in these patents are multi step processes with poor selectivity (in the range 30–50%) and require difficult high cost adipic acid recovery processes. An additional problem in all the prior art processes using molecular oxygen or air as oxidant and soluble homogeneous catalysts is the necessity to recover or dispose off the soluble metal catalysts that are used in such processes. Hence an air oxidation process that provides good yields of adipic acids free of significant byproducts, such as succinic, glutaric and caproic acids and using a solid oxidation catalyst will be highly desirable.

There have been many references in the prior art, to the one step molecular oxygen oxidation of cyclohexane to adipic acid. Japanese patent No. 45-16444 claims the oxidation of cyclohexane in acetic acid using cobalt acetate and acetaldehyde as catalysts at 80° C., oxygen at 225 psi, giving a conversion of 96% and a selectivity to adipic acid of 70%. British patent 1,143,213 claims the oxidation of cyclohexane at 114 to 119° C., 250 psi in acetic and propionic acid using manganese stearate as catalyst. U.S. Pat. No. 4,263,453 claims oxidation of cyclohexane at 95° C., 300 psi in acetic acid containing a little water and using cobalt acetate as catalyst giving a conversion of 92% and a selectivity to adipic acid of 80%. Until now however the seemingly attractive direct oxidation routes using molecular oxygen have not proven to be commercially and environmentally viable because of the soluble metal catalysts, such as cobalt acetate and cobalt napthanete used therein, as well as the low conversion (3–5%) and selectivity (30–50%) obtained in such processes. A review of the known single stage oxidation processes using catalysts for the preparation of adipic acid from cyclohexane are discussed by K. Tanaka et al in the journals Chemtech, 555–559 (1974) and Hydrocarbon Processing, 53,114–120 (1974). Additional references for the singlestep direct oxidation of cyclohexane to adipic acid using soluble homogeneous catalysts include U.S. Pat. Nos. 31,608; 2,589,648; 4,032,569; 4,263,453; 4,158,739; 5,321, 157; as well as the article by G. N. Kulsrestha et al in Chem. Tech. Biotechnol, 50,57–65 (1991).

The use of solid catalyst in the oxidation of cyclohexane to adipic acid is known in the prior art. F. T. Starzyk et al. reported in the journal "Studies in Surface Science and Catalysis;, vol. 84, pages 1419–1424 (1994) that using tertiarybutylhydroperoxide, but not molecular oxygen, as the source of oxygen and iron phthalocyanine encapsulated in Y zeolite as the catalyst, cyclohexane could be oxidised to adipic acid. One significant drawback of this process was the very slow rates of oxidation of cyclohexane thereby rendering the process commercially not attractive. FIG. 2 of the article of Starzyk et al mentioned hereinabove, for example, teaches that 300 hours of reaction time are needed to achieve a cyclohexane conversion of about 35% at 60° C. Moreover, significant quantities of adipic acid started appearing in the liquid product only after about 600 hours, the major products being cyclohexane and hydroxy ketone upto this time. Kraushtaar et al in European patent 519,569 (1992) and Lin, S. S. and Weng, H. S. in the Journal of Applied Catalysis, vol. A (105) pages 229 (1993) have claimed the use of a cobalt-substituted aluminophosphate-5 as a heterogeneous catalyst for the autoxidation of cyclohexane in acetic acid as solvent. The intermediate cyclohexanol is converted to the more stable cyclohexylacetate. Hence, this system suffers from the inherent disadvantages of requiring acetic acid solvent and separate hydrolysis and dehydrogenation steps. R. A. Sheldon et al have recently claimed in international patent PCT/NL 94/6319 (1994) and in the article in Journal of Catalysis, vol. 153, pages 1–8 (1995) that chromium substituted aluminophosphate-5 is a heterogeneous catalyst for the oxidation of cyclohexane at 115–130° C., 75 psi $O_2$ and 300 psi air in the presence of a small amount of an alkyl hydroperoxide initiator to yield cyclohexanone as the major product. Cyclohexanol conversion levels were in the range, 3–10% wt. Cyclohexanone and cyclohexanol, the former in predominant proportions, were the main products. Significant quantities of by-products, mainly, dibasic acids like succinic, glutaric and adipic acids were also produced due to the high temperatures of the reaction.

It is thus evident that there is a need for the development of a process for the oxidation of cyclohexane to adipic acid in significant yields (at least 10–15% wt, for example) and using solid, recyclable catalysts and operating at a low enough temperature to avoid the production of undesirable by-products like succinic, glutaric, caproic and hydroxy caproic acids.

SUMMARY OF THE INVENTION

Due to our continued research in this area we observed that the encapsulated organomanganese complexes used as catalysts are solids insoluble in cyclohexane or the reaction products arising from oxidation of cyclohexane. Therefore they do not undergo any aggregation or change of phase during the oxidation wherein such changes are known to lead to catalyst deactivation problems.

We have found that the oxidation stability as well as the catalytic activity of the metal salens used as catalysts in the oxidation of clyclohexane are enhanced by replacing the ring hydrogens form the salens by electron withdrawing groups like the halogens or nitro groups thereby rendering the metal ions easier to reduce, leading to an improved oxidation activity and stability of the catalysts during the reaction.

There are a total of 8 ring hydrogen atom positions on such salen molecules which can be in principle, be substituted by other substituents. We have observed that when some or all of the hydrogen atoms of the said salens are substituted by one or more electron withdrawing groups such as halogen, nitro groups or mixture of such group, there is substantial improvement in selectivity and conversion to adipic acid.

Salen type Schiff bases are planar partially of fully conjugated systems which serve as tetradenate ligands. Metallic cations can be easily accommodated at the center of these systems with the two oxygens and two nitrogens as the ligating atoms. etal containing Schiff bases of salen type chelates are useful as chemical reagent of a catalytic nature more particularly in directing certain oxidative process.

It is, therefore, an object of the present invention to provide a process for the preparation of adipic acid by the oxidation of cyclohexane using a catalyst which would remain in the solid state at the end of the oxidation reaction thereby facilitating the easy separation, recovery and recycle of the catalyst from the reaction products without having any adverse impact on the environment.

Another object of the present invention is to provide an improved process whereby the yield of adipic acid would be higher, in the range of 10 to 25%, than in the prior art processes. Yet another object of the present invention is to provide an improved process for the preparation of adipic acid at a moderate temperature wherein a large number of byproducts due to thermal oxidation of cyclohexane, cyclohexanol, cyclohexanone and adipic acid reactions are not generated.

Yet another object of the present invention was to provide a solid catalyst for the oxidation of cyclohexane to adipic acid by the zeolite encapsulated salen type manganese complexes and to provide a catalytic environment which bridge the gap between homogeneous and heterogeneous catalysis. Encapsulated complexes are free to move within the confines of the zeolite cavities but are prevented from leaching by restrictive pore openings and the zeolite cages retards the formation of dimeric species and hence enhances the reversibilty of the oxygen transfer. High selectivity and activity of the zeolite encapsulated complexes show their importance in catalysis.

An advantageous feature of the present process is that the products can be readily separated from the catalyst by filtration or encapsulation.

Another advantageous feature of the present process is that the life time of the catalysts are increased by its encapsulation since degradation pathways involving reactions such as dimerization of catalyst can be prevented.

Accordingly, the present invention provides an improved process for the oxidation of cyclohexane to adipic acid which comprises reacting cyclohexane with air in the presence of a solid catalyst containing of an encapsulated salen or substituted salen complex wherein some of the hydrogen atoms of the said organomanganese complex have been substituted by one or more electron withdrawing groups, at a temperature in the range of 20 to 110° C. at a pressure in the range of 50 to 1000 psi, in the presence or absence of solvents, with or without a promoter and isolating the adipic acid formed by conventional methods, such as filtration and centrifugation.

DETAILED DISCLOSURE

In an embodiment of the present invention, the organomanganese complex may contain N,N'-bis (salicylaldehyde/substituted salicylaldehyde) ethylenediimine(salen), N,N'-bis(salicylaldehyde/ substituted salicylaldehyde) 1,3-propylenediimine(saltin), N,N'-bis(salicylaldehyde/substituted salicylaldehyde) 1,2-phenylenediimine (salophen), N,N'-bis(salicylaldehyde/ substituted salicylaldehyde) 1,2-cyclohexane diimine (salcyhexen).

In another embodiment the complexes may be encapsulated in various molecular sieves such as silica, alumina, aluminosilicates or molecular sieves, such as zeolites.

In yet another embodiment of present invention the electron withdrawing groups attached to the organotransition metal complex may be may from the halogens, (fluorine, chlorine, bromine) and nitro groups.

In a preferred embodiment of the present invention, the oxidation of cyclohexane by air is catalysed by the halogen or nitro substituted salen, saltin, salophen or cyclohexane complexes of manganese.

In yet another embodiment of the present invention, the source of oxygen can be pure oxygen gas, air or a mixture of oxygen and an inert gas diluent like nitrogen, or molecular oxygen.

In yet another embodiment of the present invention, the solvent used in the oxidation reaction may be selected from acetonitrile, acetone, benzene or any other organic solvent which is inert under the oxidation reaction conditions. In other embodiment of the present invention, the promoter may be selected from alkyl hydroperoxide and dialkylperoxide, cyclohexyl hydroperoxide, cumyl hydroperoxide, tertiary butyl hydroperoxide.

In yet another embodiment the concentration of the promoter may not exceed 1% by weight of cyclohexane and more preferably 0.1% by weight of cyclohexane.

In yet another embodiment of the present invention, the organomanganese complex may be encapsulated in a solid matrix which may include inorganic oxide like silica, alumina, molecular sieves, zeolites as well as organic polymeric materials, like polystyrene.

In a still another embodiment of the process of the present invention, the oxidation reaction can be carried out at temperatures ranging between 20° C. to 120° C.

In a feature of the invention the suitable solvent which would have a high solubility for $O_2$ and, in addition, maintain the oxidation products like adipic acid in the dissolved state during the course of the reaction, thereby facilitating the separation of the said adipic acid from the solid catalysts. Suitable solvents for such use include acetonitrile, methanol, water, butanol and cyclohexanol. In the process of the present invention, the oxidation of cyclohexane to adipic acid proceeds via the intermediates cyclohexanol and cyclohexanone. Hence, if the oxidation to adipic acid is incomplete, the product mixture after the reaction may contain significant quantities of cyclohexanol and cylohexanone. The cyclohexanol and cyclohexanone obtained as intermediates in the oxidation of cyclohexane to adipic acid may either be recycled back to the cyclohexane oxidation zone or be converted to other valuable products, like nylon-6.

The process of the present invention is described hereinabove with reference to examples which are illustrative only and should not be construed to limit the scope of the present invention in any manner.

EXAMPLE 1

20 g of cyclohexane, 10 g of solvent, 0.5 g of [N,N'-bis(salycylaldehyde)ethylenediimine]manganese(III)chloride and 0.3 g of tertiary butyl hydroperoxide as a promoter was taken in an autoclave and pressurized with air at 600 psi. The reaction mixture was stirred at 110° C. for 22 hours. At the end of the reaction the solvent and cyclohexane layer was separated and 10 ml of methanol was added to the products (unreacted cyclohexane, cyclohexanol, cyclohexanone and adipic acid) which were then separated from the solid catalyst by centrifugation and analyzed by gas chromatography using a carbo wax column and flame ionization detector (FID). The identity of the products was confirmed by GC mass spectroscopy using standard compounds. The conversion of cyclohexane was 13% wt and the adipic acid was 4% wt.

EXAMPLE 2

In an autoclave, 30 g of cyclohexane, 0.5 g of encapsulated solid [N,N'-bis(salicylaldehyde/and 3,5-mono or di substituted chloro, bromo or nitro salicylaldehyde) ethylenediimine]manganese(III)chloride and 0.3 g of tertiary butyl hydroperoxide as a promoter were filled and pressurized with air at 600 psi. The temperature of the reaction mixture maintained at 110° C. with stirring. At the end of the reaction, 10 ml of methanol was added to the products (unreacted cyclohexane, cyclohexanol, cyclohexanone and adipic acid) which were then separated from the solid catalyst by centrifugation and analyzed by gas chromatography using a carbowax column and flame ionization detector(FID). The identity of the products was confirmed by GC mass spectroscopy using standard compounds. The results are shown in table 1.

EXAMPLE 3

In an autoclave, 30 g of cyclohexane, 0.5 g of encapsulated solid {N,N'-bis(salicylaldehyde/and 3,5-mono or di substituted chloro, bromo or nitro salicylaldehyde) 1,3-propylenediimine}manganese(III)chloride and 0.3 g of tertiary butyl hydroperoxide as a promoter were taken and pressurized with air at 600 psi. The reaction mixture was stirred at 110° C. At the end of the reaction, 10 ml of methanol was added to the products (unreacted cyclohexane, cyclohexanol, cyclohexanone and adipic acid) which were then separated from the solid catalyst by centrifugation and analyzed by gas chromatography using a carbowax column and flame ionization detector (FID). The identity of the products was confirmed by GC mass spectroscopy using standard compounds. The results are tabulated in table 1.

EXAMPLE 4

In an autoclave, 30 g of cyclohexane, 0.5 g of encapsulated solid [N,N'-bis(salicylaldehyde/and 3,5-mono or disubstituted chloro, bromo or nitro salicylaldehyde) 1,2-phenylenediimine]manganese(III)chloride and 0.5 g of tertiary butyl hydroperoxide as a promoter filled and pressurized with air at 600 psi. The reaction temperature was maintained at 110° C. with stirring. At the end of the reaction, 10 ml of methanol was added to the products (unreacted cyclohexane, cyclohexanol, cyclohexanone and adipic acid) which were then separated from the solid catalyst by centrifugation and analysed by gas chromatography using a carbowax column and flame ionization detector (FID). The identity of the products was confirmed by GC mass spectroscopy using standard compounds. The results are presented in table 1.

EXAMPLE 5

In an autoclave, 30 g of cyclohexane, 0.5 g of encapsulated solid [N,N'-bis(salicylaldehyde/and 3,5 mono or disubstituted chloro, bromo or nitro salicylaldehyde) 1.2-cyclohexanediimine]manganese(III)chloride and 0.3 g of tertiary butyl hydroperoxideas a promoter were taken and was filled with air at 600 psi pressure. The reaction temperature was monitered at 110° C. with constant stirring. At the end of the reaction, 10 ml of methanol was added to the products (unreacted cyclohexane, cyclohexanol, cyclohexanone and adipic acid) which were then separated from the solid catalyst by centrifugation and analyzed by gas chromatography using a carbowax column and flame ionization detector(FID). The identity of the products was confirmed by GC mass spectroscopy using standard compounds. The results are tabulated in table 1.

Table 1 indicates the wt % conversion of cyclohexane, wt % yield of adipic acid and the wt % yield of cyclohexanol plus cyclohexanone when using different organomanganese complexes as catalysts in acetonitrile solvent as medium and using the conditions mentioned herein above (Examples 2–5)

TABLE 1

| In wt % | Ex-2 Salen | Ex-3 Saltin | Ex-4 Salophen | Ex-5 Salcyhexen |
|---|---|---|---|---|
| Converted cyclohexane. | 13 | 12 | 13 | 12 |
| Yield of adipic acid | 4' | 3 | 5 | 4 |
| Yield of cyclohexanone plus cyclohexanol | 9 | 9 | 8 | 8 |

EXAMPLE 6

In an autoclave 20 g of cyclohexane, 10 g of solvent, 0.5 g of encapsulated solid [N,N'-bis(salicylaldehyde) ethylenediimine]manganese(III)chloride and 0.3 g of tertiary butyl hydroperoxide as a promoter were taken and air was filed at 600 psi pressure. The reaction mixture was kept on stirring at 110° C. At the end of the reaction, the two layers formed was separated and analyzed independently by the addition of methanol to the products (unreacted cyclohexane, cyclohexanol cyclohexanone and adipic acid). The solid catalyst was separated from the reaction mixture by centrifugation and the products were analyzed by gas chromatography using a carbowax column and flame ionization detector (FID). The identity of the products was confirmed by GC mass spectroscopy using standard compounds. The results are given in table 2.

EXAMPLE 7

20 g of cyclohexane, 10 g of solvent 0.5 g of encapsulated solid [N,N'-bis(salicylaldehyde)1,3-propylenediimine] manganese(III)chloride and 0.3 g of tertiary butyl hydroperoxide as a promoter were filled in an autoclave and pressurized with air at 600 psi. The reaction mixture was kept on stirring at 110° C. At the end of the reaction, the two layers formed was separated and 10 ml of methanol was added to the products (unreacted cyclohexane, cyclohexanol, cyclohexanone and adipic acid) which were then separated from the solid catalyst by centrifugation and analyzed by gas chromatography using a carbowax column and flame ionization detector (FID). The identity of the products was confirmed by GC mass spectroscopy using standard compounds. The results are presented in table 2.

EXAMPLE 8

20 g of cyclohexane, 10 g of solvent, 0.5 g of encapsulated solid [N,N'-bis(salicylaldehyde) 1,2-phenylenediimine] manganese(III)chloride and 0.3 g of tertiary butyl hydroperoxide as a promoter were taken in an autoclave and pressurized with air at 600 psi. The temperature of the reaction mixture was maintained at 110° C. with continuous stirring. At the end of the reaction, the cyclohexane and solvent layers formed was separated and 10 ml of methanol was added to the products (unreacted cyclohexane, cyclohexanol, cyclohexanone and adipic acid) which were then separated from the solid catalyst by centrifugation and analyzed by gas chromatography using a carbowax column and flame ionization detector (FID). The identity of the products was confirmed by GC mass spectroscopy using standard compounds. The results are tabulated in table 2.

EXAMPLE 9

An autoclave was charged with 20 g of cyclohexane, 10 g of solvent, 0.5 g of encapsulated solid [N,N'-bis(salicylaldehyde) 1,2-cyclohexanediimine]manganese(III) chloride and 0.3 g of tertiary butyl hydroperoxide as a promoter and finally air was pressurized at 600 psi. The mixture was stirred at 110° C. for 22 hours. After completion of the reaction, the solvent and cyclohexane layer formed was separated and added 10 ml of methanol to the obtained liquid mixture (unreacted cyclohexane, cyclohexanol, cyclohexanone and adipic acid) which were then separated from the solid catalyst by centrifugation and analyzed by gas chromatography using a carbowax column and flame ionization detector (FID). The identity of the products was confirmed by GC mass spectroscopy using standard compounds. The results are shown in table 2.

EXAMPLE 10

In an autoclave, 20 g of cyclohexane, 10 g of solvent, 0.5 g of encapsulated solid [N,N'-bis(5-halogen substituted salicylaldehyde)ethylendediimine]manganese(III)chloride and 0.3 g of tertiary butyl hydroperoxide as a promoter were taken and pressurized with air at 600 psi. The reaction mixture was constantly stirred at 110° C. for 22 hours. After completion of the reaction, the solvent and cyclohexane layer formed was separated and added 10 ml of methanol to the product mixture(unreacted cyclohexane, cyclohexanol, cyclohexanone and adipic acid) which were then separated from the solid catalyst and analyzed by gas chromatography using a carbowax column and flame ionization detector (FID). The identity of the products was confirmed by GC mass spectroscopy using standard compounds. The results are presented in table 2.

EXAMPLE 11

In an autoclave, 20 g of cyclohexane, 10 g of solvent, 0.5 g of encapsulated solid [N,N'-bis(5-halogen substituted salicylaldehyde) 1,3-propylenediimine]manganese(III) chloride and 0.3 g of tertiary butyl hydroperoxide as a promoter were charged with air at 600 psi pressure. The reaction mixture was continuously stirred at 110° C. for 22 hours. At the end of the reaction, the solvent and cyclohexane layer formed was separated and added 10 ml of methanol to the products (unreacted cyclohexane, cyclohexanol, cyclohexanone and adipic acid) which were then separated from the solid catalyst by centrifugation and analyzed by gas chromatography using a carbowax column and flame ionization detector(FID). The identity of the products was confirmed by GC mass spectroscopy using standard compounds. The results are tabulated in table 2.

EXAMPLE 12

In an autoclave, 20 g of solvent, 10 g of solvent, 0.5 g of encapsulated solid [N,N'-bis(5-halogen substituted salicylaldehyde) 1,2 phenylenediimine]manganese(III) chloride and 0.3 g of tertiary butyl hydroperoxide as a promoter were charged with air at 600 psi pressure. The reaction mixture was stirred constantly at 110° C. for 22 hours. At the end of the reaction, the solvent and cyclohexane layer formed was separated and added 10 ml of methanol to the products (unreacted cyclohexane, cyclohexanol, cyclohexanone and adipic acid) which were then separated from the solid catalyst by centrifugation and analyzed by gas chromatography (Shimadzu GC 14B) using a carbowax column and flame ionization detector(FID). The identity of the products were confirmed by GC mass spectroscopy using standard compounds. The results are shown in table 2.

EXAMPLE 13

20 g of cyclohexane, 10 g of solvent, 0.5 g of encapsulated solid [N,N'-bis(5-halogen substituted salicylaldehyde)1,2-cyclohexanediimine]manganese(III)chloride and 0.3 g of tertiary butylhydroperoxide as a promoter were filled in an autoclave and pressurized with air at 600 psi. The reaction mixture was stirred at 110° C. for 22 hours. After completion of the reaction,the solvent and cyclohexane layer formed was separated and added 10 ml of methanol to the products (unreacted cyclohexane, cyclohexanol, cyclohexanone and adipic acid) which were then separated from the solid catalyst by centrifugation and analyzed by gas chromatography using a carbowax column and flame ionization detector (FID). The identity of the products were confirmed by GC mass spectroscopy using standard compounds. The results are tabulated in table 2.

EXAMPLE 14

20 g of cyclohexane, 10 g of solvent, 0.5 g of encapsulated solid [N,N'-bis(5-nitro or and 3.5-dinitrosalicylaldehyde)1,2-ethylenediimine]manganese(III)chloride and 0.3 g of tertiary butyl hydroperoxide as promoter were charged in an autoclave and air was filled at 600 psi pressure. The reaction mixture was stirred at 110° C. for 22 hours. After completion of the reaction, the solvent and cyclohexane layer formed was separated and added 10 ml of methanol to the products (unreacted cyclohexane, cyclohexanol, cyclohexanone and adipic acid) which were then separated from the solid catalyst by centrifugation and analyzed by gas chromatography using a carbowax column and flame ionization detector(FID). The identity of the compounds were confirmed by GC mass spectroscopy using standard compounds. The results are shown in table 2.

EXAMPLE 15

In an autoclave, 20 g of cyclohexane, 10 g of solvent, 0.5 g of encapsulated solid [N,N'-bis(5-nitro or and 3,5-dinitrosalicylaldehyde) 1,3-propylenediimine]manganese (III)chloride and 0.3 g of tertiary butyl hydroperoxide as a promoter were charged with air at 600 psi pressure. The reaction mixture was continuously stirred at 110° C. for 22 hours. At the end of the reaction, the solvent and cyclohexane layer formed was separated and added 10 ml of methanol to the products (unreacted cyclohexane, cyclohexanol, cyclohexanone and adipic acid) which were then separated from the solid catalyst by centrifugation and analyzed by gas chromatography using a carbowax column and flame ionization detector(FID). The identity of the products was confirmed by GC mass spectroscopy using standard compounds. The results are presented in table 2.

EXAMPLE 16

In an autoclave, 20 g of cyclohexane, 10 g of solvent, 0.5 g of encapsulated solid [N,N'-bis(5-nitro or and 3,5-dinitrosalicylaldehyde) 1,2-phenylenediimine]manganese (III)chloride and 0.3 g of of tertiary butyl hydroperoxide as a promoter were charged with air at 600 psi pressure. The reaction mixture was continuously stirred at 110° C. for 22 hours. After completion of the reaction, the solvent and cyclohexane layer formed was separated and added 10 ml of methanol to the products (unreacted cyclohexane, cyclohexananol, cyclohexanone and adipic acid) which were then separated from the solid catalyst by centrifugation and analyzed by gas chromatography using a carbowax column and flame ionization detector (FID). The identity of the products was confirmed by GC mass spectroscopy using standard compounds. The results are shown in table 2.

EXAMPLE 17

In an autoclave, 20 g of cyclohexane, 10 g of solvent, 0.5 g of encapsulated solid [N,N'-bis(5-nitro or and 3,5-dinitrosalicylaldehyde)1,2-cyclohexanediimine]manganese (III)chloride and 0.3 g of tertiary butyl hydroperoxide as a promoter were filled and pressurized with air at 600 psi. The reaction mixture was constantly stirred at 110° C. for 22 hours. At the end of the reaction the solvent and cyclohexane layer was separated and added 10 ml of methanol to the products (unreacted cyclohexane, cyclohexanol, cyclohexanone and adipic acid) which were then separated from the solid catalyst by centrifugation and analyzed by gas chromatography using a carbowax column and flame ionization detector (FID). The identity of the products was confirmed by GC mass spectroscopy using standard compounds. The results are presented in table 2.

EXAMPLE 18

An autoclave was charged with 20 g of cyclohexane, 10 g of solvent, 0.5 g of encapsulated solid [N,N'-bis (3,5-dihalogen substituted salicylaldehyde)ethylenediimine] manganese(III)chloride and 0.3 g of tertiary butyl hydroperoxide as a promoter and finally filled with air at 600 psi pressure. The mixture was stirred at 110° C. for 22 hours. After the completion of the reaction, the solvent and cyclohexane layer formed was separated and added 10 ml of methanol to the obtained liquid mixture (unreacted cyclohexane, cyclohexanol, cyclohexanone and adipic acid) which were then separated by centrifugation and analyzed by gas chromatography using a carbowax column and flame ionization detector(FID). The identity of the products was confirmed by GC mass spectroscopy using standard compounds. The results are shown in table 2.

EXAMPLE 19

20 g of cyclohexane, 10 g of solvent, 0.5 g of encapsulated solid [N,N'-bis(3,5-dihalogen substituted salicylaldehyde) 1,3-propylendeiimine]manganese(III)chloride and 0.3 g of tertiary butyl hydroperoxide as a promoter were filled in an autoclave and pressurized with air at 600 psi. The reaction temperature was maintained at 110° C. with stirring for 22 hours. At the end of the reaction the solvent and cyclohexane layer formed was separated and added 10 ml of methanol to the products(unreacted cyclohexane, cyclohexanol, cyclohexanone and adipic acid) which were separated by centrifugation and analyzed by gas chromatography using a carbowax column and flame ionization detector(FID). The identity of the products were confirmed by GC mass spectroscopy using standard compounds. The results are tabulated in table 2.

EXAMPLE 20

20 g of cyclohexane, 10 g of solvent, 0.5 g of encapsulated solid [N-N' bis(3,5dihalogen substituted salicylaldehyde)1, 2-phenylenediimine]manganese(III)chloride and 0.3 g of tertiary butyl hydroperoxide as a promoter were filled in an autoclave and pressurized with air at 600 psi. The temperature of the reaction mixture was maintained at 110° C. with constant stirring. At the end of the reaction, the solvent and cyclohexane layer was separated and added 10 ml of methanol to the products (unreacted cyclohexane, cyclohexanol, cyclohexanone and adipic acid) which were separated by centrifugation and analyzed by gas chromatography using a carbowax column and flame ionization detector (FID).The identity of the products were confirmed by GC mass spectroscopy using standard compounds. The results are shown in table 2.

EXAMPLE 21

An autoclave was charged with 20 g of cyclohexane, 10 g of solvent, 0.5 g of encapsulated solid [N,N'-bis(3, 5dihalogen substituted salicylaldehyde)1,2-phenylenediimine]manganese(III)chloride and 0.3 g of tertiary butyl hydroperoxide as a promoter. Autoclave was pressurized with air at 600 psi and stirred at 110° C. for 22 hours. After completion of the reaction, the solvent and the cyclohexane layer was separated and added 10 ml of methanol to the products (unreacted cyclohexane, cyclohexanol cyclohexanone and adipic acid) which were separated by centrifugation and analyzed by gas chromatography using a carbowax column and flame ionization detector (FID). The identity of the products was confirmed by GC mass spectroscopy using standard compounds. The results are presented in table 2.

Table 2 indicates the wt. % conversion of cyclohexane, wt. % yield of adipic acid and the wt. % yield of cyclohexanol plus cyclohexanone when using different organomanganese complexes in acetonitrile solvent as medium and using the conditions mentioned herein above (Examples 6–21).

TABLE 2

| Example + | Catalyst | Cyclohexane Conv. (wt %) | Adipic acid (wt %) | Yield of cyclohexanol cyclohexanone (wt %) |
|---|---|---|---|---|
| 6 | Salen | 18 | 07 | 10 |
| 7 | Saltin | 18 | 08 | 09 |
| 8 | Salophene | 17 | 08 | 08 |
| 9 | Salicyhexene | 19 | 08 | 09 |
| 10 | 5-Brsalen | 20 | 11 | 09 |
| 11 | 5-Brsaltin | 19 | 09 | 10 |
| 12 | 5-Brsalophene | 18 | 09 | 09 |
| 13 | 5-Brsalicyhexene | 18 | 08 | 10 |
| 14 | 5-$NO_2$salen | 18 | 08 | 09 |
| 15 | 5-$NO_2$saltin | 16 | 08 | 08 |
| 16 | 5-$NO_2$salophene | 17 | 08 | 09 |
| 17 | 5-$NO_2$salcyhexane | 20 | 09 | 09 |
| 18 | 3,5-$Cl_2$salen | 21 | 11 | 10 |
| 19 | 3,5-$Cl_2$saltin | 19 | 09 | 10 |
| 20 | 3,5-$Cl_2$salophene | 21 | 10 | 10 |
| 21 | 3,5-$Cl_2$salcyhexene | 19 | 10 | 09 |

EXAMPLE 22

In an autoclave 15 g of cyclohexane, 15 g of solvent, 0.5 g of encapsulated solid [N,N'-bis(5-halogen substituted salicylaldehyde) ethylenediimine]manganese(III)chloride and 0.3 g of tertiary butyl hydroperoxide as a promoter were charged with air at 600 psi pressure. The reaction mixture was stirred constantly at 110° C. for 22 hours. At the end of the reaction, the solvent and cyclohexane layer formed was separated and added 10 ml of methanol to the products (unreacted cyclohexane, cyclohexanol, cyclohexanone and adipic acid) which were then separated from the solid catalyst by centrifugation and analyzed by gas chromatogragphy using a carbowax column and flame ionization detector (FID). The identity of the products was confirmed by GC mass spectroscopy using standard compounds. The conversion of cyclohexane was 16% wt. and the adipic acid was 6% wt.

We claim:

1. A process for the oxidation of cyclohexane to adipic acid, which comprises contacting cyclohexane with oxygen in the presence of a solid catalyst containing an encapsulated substituted salen metal complex wherein some of the hydrogen atoms of said complex were substituted by one or more electron withdrawing groups, in the presence or absence of solvents, with or without a promoter, wherein said encapsulated metal complex is selected from the group consisting of: N,N'-bis(salicylaldehyde/substituted salicylaldehyde) ethylenediimine (salen), N,N'-bis(salicylaldehyde/ substituted salicylaldehyde) 1,3-propylenediimine (saltin), N,N'-bis(salicylaldehyde/substituted salicylaldehyde 1,2-phenylenediimine (salophen), N,N'-bis(salicylaldehyde/ substituted salicylaldehyde) 1,2-cyclohexanediimine (salcyhexen) and isolating the formed adipic acid.

2. The process of claim 1, wherein said oxidation is carried out at a temperature of from 20° C. to 120° C.

3. The process of claim 2, wherein said oxidation is carried out at a pressure of from 50 psi to 1000 psi.

4. The process of claim 1, wherein said substituted salen metal complex is at least one of substituted salen, saltin, salophen, and salcyhexen.

5. The process of claim 4, wherein said metal complex is an organomanganese complex.

6. The process of claim 1, wherein said step of isolating the adipic acid is carried out by filtration or by centrifuging.

7. The process of claim 1, wherein the metal complex is encapsulated in a solid matrix.

8. The process of claim 7, wherein said solid matrix is selected from the group consisting of silica, alumina, at least one aluminosilicate, at least one zeolite, and an organic polymer.

9. The process of claim 1, wherein said electron withdrawing group is one or more of at least one halogen, and nitro groups.

10. The process of claim 1, wherein the source of said oxygen is pure oxygen gas, air, or a mixture of oxygen and an inert gas diluent therefor.

11. The process of claim 10, wherein said inert gas diluent is nitrogen.

12. The process of claim 1, wherein said solvent is one or more of acetonitrile, acetone, benzene, or another organic solvent that is inert under oxidizing conditions.

13. The process of claim 1, wherein said promoter is selected from the group consisting of an alkyl hydroperoxide, a dialkylperoxide, cyclohexyl hydroperoxide, cumyl hydroperoxyde, and tert.-butyl hydroperoxide.

14. The process of claim 1, wherein the maximum concentration of said promoter is 1% wt based on cyclohexane.

15. The process of claim 7, wherein the solid matrix is a molecular sieve.

16. The process of claim 8, wherein the organic polymer is polystyrene.

* * * * *